United States Patent [19]

Halm et al.

[11] Patent Number: 4,764,631

[45] Date of Patent: Aug. 16, 1988

[54] PREPARATION OF CYCLOPOLYDIORGANOSILOXANES VIA VAPOR PHASE REARRANGEMENT

[75] Inventors: Roland L. Halm, Madison, Ind.; Sidney A. Hansen, Beaverton; Charles E. Neal, Jr., Midland, both of Mich.

[73] Assignee: Dow Corning Corporation, Midland, Mich.

[21] Appl. No.: 144,287

[22] Filed: Jan. 15, 1988

[51] Int. Cl.[4] .................................. C07F 7/08;
[52] U.S. Cl. ..................................... 556/460
[58] Field of Search ........................ 556/460, 461

[56] References Cited

U.S. PATENT DOCUMENTS

| | | | |
|---|---|---|---|
| 2,438,478 | 3/1948 | Hyde | 260/448.2 |
| 2,455,999 | 12/1948 | Hyde | 260/448.2 |
| 2,816,124 | 12/1957 | York | 556/460 |
| 2,860,152 | 11/1958 | Fletcher | 556/460 |
| 2,884,432 | 4/1959 | Gordon | 260/448.2 |
| 2,979,519 | 4/1961 | Pierce et al. | 260/448.2 |
| 3,484,469 | 12/1969 | Guinet et al. | 260/448.2 |
| 3,558,681 | 1/1971 | Kutznetsova et al. | 260/448.2 |
| 3,607,898 | 9/1971 | Macher | 260/448.2 |
| 3,846,464 | 11/1974 | Razzano | 556/460 |
| 3,989,733 | 11/1976 | Okamoto et al. | 260/448.2 |
| 4,111,973 | 9/1978 | Bluestein | 260/448.2 |
| 4,197,251 | 4/1980 | Hirakawa | 260/448.2 |
| 4,412,081 | 10/1983 | Williams | 556/460 |
| 4,556,726 | 12/1985 | Reedy et al. | 556/460 |
| 4,620,023 | 10/1986 | Kreuzer et al. | 556/460 |
| 4,689,420 | 8/1987 | Baile et al. | 556/460 |

OTHER PUBLICATIONS

Carmichael et al., *J. Phys. Chem.*, 71 (1967), pp. 2011–2015.
Hunter et al., *J. Am. Chem. Soc.*, 68 (1946), pp. 667–672.
Rode et al., *Vysokomal. soyed. All.*, 11 (1969), pp. 1733–1744.
Davidson et al., *Chemical Communications* (1971), pp. 251–252.
Gusel'nikov et al., *Bull. Acad. Sci., USSR*, 20 (1971), pp. 71–75.

*Primary Examiner*—Paul F. Shaver
*Attorney, Agent, or Firm*—Carl A. Yorimoto

[57] ABSTRACT

A process for preparing a product cyclopolydiorganosiloxane, $(R_2SiO)_c$. The process comprises (A) vaporizing a feed cyclopolydiorganosiloxane material, $(R_2SiO)_x$; (B) passing the vapors from (A) through a heated bed of a solid catalyst, the catalyst comprising an alkali metal compound; (C) controlling pressure and temperature in the heated catalyst bed to favor formation of $(R_2SiO)_c$ in an equilibrating mixture with other cyclopolydiorganosiloxanes; and (D) recovering an amount of the product cyclopolydiorganosiloxane, $(R_2SiO)_c$, which is substantially increased from the amount present in the feed cyclopolydiorganosiloxane material.

16 Claims, No Drawings

PREPARATION OF CYCLOPOLYDIORGANOSILOXANES VIA VAPOR PHASE REARRANGEMENT

BACKGROUND OF THE INVENTION

This invention relates to preparation and isolation of essentially pure cyclopolydiorganosiloxane species. More specifically, this invention relates to the preparation of the cyclopolydiorganosiloxanes from the vapor-phase rearrangement of other cyclopolydiorganosiloxanes or mixtures thereof.

For the purposes of the instant invention, "cyclopolydiorganosiloxanes" or "$D_c$" are organosiloxanes having the formula.

$$(R_2SiO)_c,$$

wherein each R is an alkyl, alkenyl, aryl, or alkaryl group, and c has a value of 3 or greater.

Cyclopolydiorganosiloxanes such as cyclooctamethyltetrasiloxane, $[(CH_3)_2SiO]_4$, and mixtures thereof are critical intermediates in the silicone industry, primarily as starting monomers for polymerization. As the technology of the silicones industry has advanced, the need for the individual species of cyclopolydiorganosiloxanes has become a matter of commercial interest. As an example, the cyclotrisiloxanes, $D_3$, are of commercial interest because of their high reactivity in the formation of polymers.

Several general routes are known for the preparation of cyclopolydiorganosiloxanes. A basic process is the separation and isolation of $D_c$ from the product of hydrolysis of the corresponding diorganodihalosilane. The hydrolysis product is a mixture of $D_c$ and hydroxy endblocked linear polydiorganosiloxanes. The predominant species in the mixture of $D_c$ is the tetramer or $D_4$. One has limited flexibility in altering the mix of species within the $D_c$ mixture. To balance the need for $D_c$ beyond $D_4$ or a $D_c$ mixture, one must turn to one of the other processes that will be discussed, infra.

A second general route to $D_c$ is the liquid phase equilibration or "cracking" reaction in which mixtures of $D_c$ and/or linear polydiorganosiloxanes are reacted in the presence of a catalyst such as a base to form an equilibrium mixture of $D_c$ and linears. The $D_c$ is then removed batchwise or continuously from the equilibrium mixture by fractionation or other means of separation. In the liquid phase, the equilibrium mixture of $D_c$ to linears can be as low as 10 to 15 percent $D_c$. Dilution with solvent to a siloxane content of approximately 20 to 25 percent can result in a $D_c$ content of the siloxane mixture of 70 to 75 percent. The liquid phase equilibrium and impact of solvent are discussed in Carmichael et al., *J. Phys. Chem.*, 71(1967), pp. 2011–15.

Hunter et al., *J. Am. Chem. Soc.*, 68(1946), pp. 667–672, describe a method for preparing and isolating polydimethylsiloxanes. Hyde, U.S. Pat. No. 2,438,478, issued Mar. 23, 1948, and Hyde, U.S. Pat. No. 2,455,999, issued Dec. 14, 1948, make similar disclosure. York, U.S. Pat. No. 2,816,124, issued Dec. 10, 1957, discloses a process for preparing hexaethylcyclotrisiloxane. Fletcher, U.S. Pat. No. 2,860,512, issued Nov. 11, 1958, discloses a method for preparing cyclic polydiorganosiloxanes in the presence of a high-boiling solvent. Gordon, U.S. Pat. No. 2,884,432, issued Apr. 28, 1959, discloses a process in which triorganosiloxanes are used to cause the contents of the equilibration vessel to remain fluid and to reduce the cracking temperature. Pierce and Holbrook, U.S. Pat. No. 2,979,519, issued Apr. 11, 1961, and Bluestein, U.S. Pat. No. 4,111,973, issued Sept. 5, 1978, disclose processes for the preparation of cyclopolytrifluoropropylmethylsiloxanes. Guinet and Puthet, U.S. Pat. No. 3,484,469, issued Dec. 19, 1969, and Kuznetsova et al., U.S. Pat. No. 3,558,681, issued Jan. 26, 1971, disclose processes for the preparation of cyclopolyphenylmethylsiloxanes. Macher, U.S. Pat. No. 3,607,898, issued Sept. 21, 1971, and Razzano, U.S. Pat. No. 3,846,464, issued Nov. 5, 1974, disclose processes for the preparation of cyclopolymethylvinylsiloxanes.

Okamoto and Yanagisawa, U.S. Pat. No. 3,989,733, issued Nov. 2, 1976, discloses a combination "cracking" and rectification process in a column-type reactor which uses as the column packing an alkaline catalyst in the form of pellets or an inert material upon which the alkaline catalyst is fused. In the continuous process disclosed, linear polydiorganosiloxanes and cyclopolydiorganosiloxanes are fed to the column. The raw material polysiloxanes fed to the catalyst zone undergo rearrangement in the course of flowing down through the catalyst zone, forming the desired cyclopolydiorganosiloxanes within the liquid layer on the catalyst surface, the cyclic siloxanes leaving as a vapor.

Hirakawa and Honda U.S. Pat. No. 4,197,251, issued Apr. 8, 1980, discloses a continuous process for producing octamethylcyclotetrasiloxanes by a cracking technique in which octamethylcyclotetrasiloxane is recovered and other cyclics species are recycled to the cracking reactor. Baile et al., U.S. Pat. No. 4,689,420, issued Aug. 25, 1987, discloses a two-step process in which water is removed from the polydiorganosiloxane feed before it is equilibrated to produce the desired cyclopolydiorganosiloxanes.

In a third route to $D_c$, Reedy and Walsh, U.S. Pat. No. 4,556,726, issued Dec. 3, 1985, discloses a method for preparing decamethylcyclopentasiloxane, $D_5$, from octamethylcyclotetrasiloxane, $D_4$, by heating the $D_4$ in the presence of aqueous hydrochloric acid and a salt of a protonated amine.

The instant invention involves the preparation and isolation of specific $D_c$ species via the vapor phase rearrangement of other $D_c$ materials or mixtures thereof. Rode, et al., *Vysokomal.soyed.All*, 11(1969), pp. 1733–1744, describes study on the thermal degradation and stabilization of polydimethylsiloxanes. Rode et al., studied the degradation of hydroxy-endblocked and trimethylsilyl-endblocked linear polydimethylsiloxanes. Rode et al., found that heating the polydimethylsiloxanes in an inert medium or under vacuum led to the formation of $D_c$, mainly $D_3$. However, Rode et al., found that in the presence of sodium hydroxide or sulfuric acid, no traceable $D_3$ was present. Davidson and Thompson, *Chemical Communications*, (1971), pp. 251–252, discloses a study of the pyrolysis of octamethylcyclotetrasiloxane, $D_4$, in the gas phase at temperatures of about 760° to 842° K. at pressures from about 0.5 to 13 mm Hg in a static system. Davidson and Thompson found that pyrolysis of up to about 25 percent of the $D_4$ gave $D_5$ and $D_6$ as the only products. Gusel nikov et al., *Bull. Acad. Sci., USSR*, 20(1971), pp. 71–75, describes the pyrolysis of cyclodimethylsiloxanes —$D_3$, $D_4$, $D_5$, and $D_6$—at 550° C. for 3 hours. None of these references discloses the control of distribution of a cyclopolydiorganosiloxane mixture, by varying temperature and pressure, to prepare and isolate individual $D_c$ species.

SUMMARY OF THE INVENTION

The objective of the instant invention is to prepare and isolate increased quantities of essentially pure cyclopolydiorganosiloxanes —$D_3$, $D_4$, $D_5$, $D_6$, as examples. It is a further objective of the instant invention to provide a process with the flexibility to produce a wide range of individual cyclic siloxane materials in commercial volumes at the lowest cost possible.

The inventors of the instant invention have found that in the presence of an alkali metal compound, under conditions that will maintain products and reactants in a vapor state, cyclopolydiorganosiloxanes or mixtures of cyclopolydiorganosiloxanes will move toward an equilibrium mixture of cyclopolydiorganosiloxanes. The inventors of the instant invention have found that thermodynamic equilibrium controls the cyclopolydiorganosiloxane, $D_c$, distribution, where c has a value of 3 to 9. It was found that by changing the reaction parameters of temperature and pressure the $D_c$ distribution could be shifted. Thus, conditions may be altered to maximize the content of, for example, $D_3$ or $D_5$ instead of the more prevalent $D_4$.

The instant invention has the advantage over the recovery of $D_c$ from the product of hydrolysis of the corresponding diorganohalosilane that the distribution of $D_c$ in an equilibrium mixture is not fixed. The conditions of the instant invention can be altered to satisfy the demand for the particular $D_c$ specie or species needed.

The instant invention has several advantages over the liquid phase processes. As noted, supra, the equilibrium distribution for a liquid phase process is a mixture of cyclic and linear siloxanes. Without solvent, the linear siloxanes predominate. The maximum cyclic siloxane content attainable is approximately 75 percent at a dilution of 25 percent (or less) siloxane in solvent. Additionally, $D_4$ is normally the predominant cyclic siloxane specie. Thus, an essentially fixed distribution of cyclic siloxanes would mean handling greater quantities of siloxanes to meet the demand for the individual $D_c$ species. Further, in vaporphase rearrangement, in the absence of a liquid phase, the equilibrating siloxane mixture in the vapor is essentially all cyclic siloxanes, the distribution of cyclic siloxane species being altered by temperature and pressure within the reaction zone. Additionally, time required to approach equilibrium in a vapor-phase reactor is a matter of seconds or fraction of seconds compared to a matter of minutes or even hours for a liquid phase process. The need for solvent dilution and solvent handling and significantly longer reaction times for a liquid phase process requires significantly larger and more numerous pieces of processing equipment. Therefore, the liquid phase would be at a capital and manufacturing cost disadvantage compared to the instant invention.

Compared to the process in which octamethylcyclotetrasiloxane is converted to decamethylcyclopentasiloxane via heating in aqueous hydrogen chloride and in the presence of a salt of a protonated amine, the instant invention has the advantage of being able to alter temperature and pressure conditions to shift the distribution of the product $D_c$ mixture to produce the desired specie or species that demand requires.

In none of the references, supra, is there any suggestion or demonstration of a process in which the equilibrium distribution of cyclopolydiorganosiloxanes in the vapor-phase can be shifted significantly to species beyond $D_3$ and $D_4$ by varying conditions of temperature and pressure as in the instant invention.

DESCRIPTION OF THE INVENTION

In accordance with the instant invention, there is provided a process for the preparation and isolation of increased quantities of essentially pure cyclopolydiorganosiloxanes, the conditions of said process will be described herein. What is described, therefore, is a process for preparing a product cyclopolydiorganosiloxane, $$(R_2SiO)_c,$$

wherein each R is independently selected from a group consisting of alkyl groups, alkenyl groups, aryl groups, and alkaryl groups; and c has a value of 3, 4, 5, 6, 7, 8, or 9, said process comprising (A) vaporizing a feed material consisting of a cyclopolydiorganosiloxane having the formula, $$(R_2SiO)_x$$

wherein each R is defined above; and x is 3, 4, 5, 6, 7, 8, or 9, or a mixture of said cyclopolydiorganosiloxanes, (B) passing vapors of the feed material through a heated bed of a solid catalyst, said catalyst comprising an alkali metal compound;

(C) controlling pressure and temperature in the heated catalyst bed to favor formation of $(R_2SiO)_c$ in an equilibrating mixture with other cyclopolydiorganosiloxanes;

(D) recovering an amount of the product cyclopolydiorganosiloxane, $(R_2SiO)_c$, which is substantially increased from the amount present in the feed material.

The organic groups of the cyclopolydiorganosiloxanes are chosen from alkyl, alkenyl, aryl, and alkaryl groups. The alkyl group can be, for example, methyl, ethyl, n-propyl, trifluoropropyl, n-butyl, sec-butyl, and tert-butyl. The alkenyl group can be, for example, vinyl, allyl, propenyl, and butenyl. The aryl and alkaryl groups can be, for example, phenyl, tolyl, and benzoyl. The preferred groups are methyl, ethyl, phenyl, vinyl, and trifluoropropyl.

The cyclopolydiorganosiloxane can be, for example, $$[(CH_3)_2SiO]_3,$$

$$[(CH_3)_2SiO]_4,$$

$$[(CH_3)_2SiO]_5,$$

$$[(CH_3)_2SiO]_6,$$

$$[(CH_3)(C_2H_5)SiO]_4,$$

$$[(CH_3)(CH=CH_2)SiO]_3,$$

$$[(CH_3)(C_6H_5)SiO]_4,$$

$$[(CH_3)(F_3CCH_2CH_2)SiO]_3, \text{ and}$$

$$[(CH_3)(C_6H_5CH_2)SiO]_4.$$

An ultimate equilibrium exists between cyclic and linear polydiorganosiloxane species in the vapor and liquid phases. As noted, supra, in the absence of a solvent the equilibrating mixture in the liquid phase favors the linear polydiorganosiloxanes. In feeding a cyclopolydiorganosiloxane to an equilibration process, the presence of a liquid phase significantly reduces the amount of cyclopolydiorganosiloxanes that would be present in the total vapor and liquid phases as the system moves toward equilibrium. As noted in the examples, infra, in the absence of a liquid phase, the vapor phase consists essentially of the desirable cyclopolydiorganosiloxanes. Thus, the vapor phase equilibration of cyclopolydiorganosiloxanes essentially eliminates the retention of linear species in the reactor or the need to recycle these linear species.

As noted in the examples, infra, the instant invention provides the temperature, pressure, and catalyst conditions to alter the distribution of cyclopolydiorganosiloxane species moving toward thermodynamic equilibrium (equilibrating) in the vapor phase. As an example, for cyclopolydimethylsiloxanes, the following trends are noted:

1. The content of $[(CH_3)_2SiO]_3$ in the vapor phase is favored by temperatures greater than about 300° C. and low pressures of 10 mm Hg or less. More preferred conditions are temperature in a range from about 300° to 450° C. and pressure in a range from about 5 to 10 mm Hg.

2. The content of $[(CH_3)_2SiO]_4$ in the vapor phase is favored by temperatures of about 200° C. and moderate pressures of about 100 mm Hg.

3. The content of $[(CH_3)_2SiO]_5$ and $[(CH_3)_2SiO]_6$ in the vapor phase is favored by temperatures as close to the dew point of the equilibrating mixture as possible (approximately 200° to 250° C.) and pressure greater than about 400 mm Hg. More preferred conditions are temperature in a range from about 200° to 300° C. and pressure in a range from about 500 to 1500 mm Hg.

The catalyst can be an alkali metal compound. The alkali metal compound can be, for example, sodium hydroxide, sodium carbonate, potassium hydroxide, potassium carbonate, cesium hydroxide, or cesium carbonate. The preferred alkali metal compound is potassium hydroxide. The preferable form of the catalyst is an alkali metal compound on a carbonaceous support. As noted in the examples, infra, other solid supports were evaluated. However, only alkali metal compounds on a carbonaceous support were effective for the vapor-phase equilibration of cyclopolydiorganosiloxanes. The carbonaceous support can be, for example, activated carbon, coke, or charcoal. Further, the form of the carbonaceous support can be, for example, powder, granule, pellet, lump, or briquette.

For the catalyst in the form of an alkali metal compound on a carbonaceous support, the alkali metal compound should be present at greater than about one percent of the weight of the catalyst. More preferably, the alkali metal compound should be present in a range from about 1 to 5 percent of the weight of the catalyst. The inventors believe that alkali metal compound content of less than one weight percent of the catalyst can be effective as a catalyst; however, conversion to the desired cyclic siloxane and rate of reaction are slowed correspondingly. The inventors further believe that alkali metal compound content greater than 5 weight percent of the catalyst can be utilized; however, no benefit in conversion of cyclic siloxanes and reaction rate are anticipated. Additionally, higher levels of alkali metal compound may have a detrimental effect upon cyclopolydiorganosiloxane quality by accelerating the rate of cleavage of organic groups, resulting in increased trior tetrafunctionality of the desired cyclopolydiorganosiloxanes.

As noted, supra, temperature and pressure conditions are controlled to alter the equilibrating mixture of cyclopolydiorganosiloxanes in the vapor phase to favor a desired cyclics species. Temperature in the catalyst zone should be above the dew point of the siloxane mixture at the pressure of the system to assure that the siloxane materials in the reaction zone are in a vapor state.

Pressure in the contact/reaction zone can be as low as 5 mm Hg to favor, for example, the formation of $[(CH_3)_2SiO]_3$. Pressure can also be above atmospheric pressure to favor, for example, the formation of $[(CH_3)_2SiO]_5$ and $[(CH_3)_2SiO]_6$.

With an unsupported alkali metal compound, contact time to effect conversion of the feed cyclosiloxanes to a desired cyclosiloxane distribution, the time required for the vapors of the feed material to pass through the heated bed of a solid catalyst, may be as great as several minutes. With an alkali metal catalyst supported on a carbonaceous surface, time to reach a desired cyclosiloxane distribution can be as short as 0.5 seconds. With a supported catalyst it is preferred that contact time be in a range from about 1 to 6 seconds. Shorter contact times may be utilized, however, with proportionately less complete approach to equilibrium of the cyclopolydiorganosiloxanes. Extended contact times of greater than several seconds or several minutes may be utilized; however, the inventors believe that higher contact times adversely affect the quality of the cyclopolydiorganosiloxanes by increasing cleavage of organic groups.

The inventors have found that water has an impact upon the course of this rearrangement reaction. The rate of equilibration of the feed cyclics drops off during extended operation, if additional water is not added to the feed material. In the case of dimethylsiloxanes, feed dimethylcyclosiloxanes were found to have as much as 20 to 40 ppm free water. However, it is recognized that water content of the feed could be higher. It was found that feed material with a total water content of greater than about 50 ppm maximized the equilibration. It is preferred that the total water content of the feed material be in a range from about 50 to 100 ppm. Free water levels in the feed material greater than about 100 ppm are not seen to have further beneficial effect. Gross amounts of water could have a detrimental effect upon the catalyst by dissolving the alkali metal compound. Water content of the feed material can be controlled by either water addition or water removal. Water addition can be effected by conventional means of adding small amounts of liquid to another liquid. Additional water can also be added as a vapor or steam in a conventional manner to adding gaseous materials. Water removal can be effected by such known means as coalescence or contact with a water adsorbent material such as molecular sieves.

Additionally. the inventors have found that excess water on the surface of the catalyst before the start of a run may have a detrimental effect, apparently causing excessive cleavage of organic groups and fouling of the catalyst surface with highly branched polymers. It is preferred that the catalyst be purged with an inert gas during initial heat-up of a catalyst bed to dry the catalyst surface.

The cyclopolydiorganosiloxanes can be fed by such known methods as liquid pumping. The feeds can be vaporized by such known methods as a tank-type vaporizer, heat exchangers utilizing hot heat transfer liquid or condensing steam, and the like.

The feed vapors can be contacted with the catalyst via such conventional methods as a packed bed of solids, a fluid bed of solids, a stirred bed of solids, or the like. The packed bed of solids or the like should be provided with means for heating. Means for heating can be conventional methods such as heating a jacket around the reactor or internal heat transfer tubes within the solids with a heated liquid, gas, or condensing steam.

Controlling the temperature and pressure in the bed of solid catalyst can be effected by conventional methods. Temperature control can be effected by control of the temperature of the bed of solids or the temperature of the feed cyclopolydiorganosiloxane vapors or a combination of both. Pressure control can be conventional vacuum or pressure control. Vacuum can be generated by such means as mechanical vacuum pumps and steam or gas aspirators. Pressure control can be effected by allowing autogenous pressure to build in the reaction zone and controlling pressure with a conventional pressure control valve and controller.

The effluent from reactor, substantially increased in a desired $(R_2SiO)_c$ specie or species can be further processed to recover the desired $(R_2RiO)_c$ specie. Recovery of the desired $(R_2SiO)_c$ species can be effected by such conventional techniques as distillation. As an example, $[(CH_3)_2SiO]_3$, $[(CH_3)_2SiO]_4$, and $[(CH_3)_2SiO]_5$ can be isolated from mixtures of $[(CH_3)_2SiO]_c$ by conventional distillation to purities of greater that 95 weight percent.

So that those skilled in the art may better understand and appreciate the instant invention, the following examples are presented. These examples are presented to be illustrative and are not to be construed as limiting the claims herein.

EXAMPLE 1

An apparatus was assembled to effect the vapor phase rearrangement of cyclopolydimethylsiloxanes $(D_x)$. The reactor was a tubular reactor constructed of either quartz or metal. The entrance section of the reactor, the bottom of the reactor was packed with a support material such as glass beads. The remainder of the reactor was packed with the solid catalyst. The catalyst bed was fitted with a temperature measuring device. The reactor was enclosed in an electrically heated oven. The temperature measuring device was coupled to a temperature control device which regulated the temperature within the reactor. This was a conventional apparatus for carrying out high-temperature gas-solid reactions.

The reactor system was provided with means for operating under vacuum, atmospheric pressure, or under pressure.

The starting $D_x$ feed was metered as a liquid by a conventional positive displacement pump. The liquid feed was fed to a flash vaporizer consisting of a pipe coil in a heated bath of heat transfer fluid. The bath temperature was controlled at the desired vaporization temperature. The flow of liquid $D_x$ feed was controlled to attain the necessary residence time within the reactor.

The vapors exiting the reactor were cooled to condense the effluent materials. The liquid product was collected and analyzed. Analysis was effected by standard gas chromatographic techniques. An appropriate internal standard was used to account for all of the components of the reactor effluent.

The procedure utilized was to load the chosen solid catalyst to the reactor and then to heat the reactor and its content to 400° to 450° C. under a helium purge for at least two hours. The desired reactor temperature was set on the reactor temperature controller. and the reactor was held at the desired temperature for 30 to 60 minutes to establish thermal equilibrium under a helium purge. The helium purge was then stopped. The $D_x$ feed to the vaporizer and reactor was begun. The $D_x$ feed was continued for 10 to 15 minutes. At this time, the system was at steady state operation. Samples of the collected reactor effluent were then taken and analyzed.

Two runs were made with powdered reagent sodium carbonate $(Na_2CO_3)$. Reactor system pressure was maintained at essentially atmospheric pressure. The $D_x$ feed was essentially $D_4$. Temperature and residence time were varied. These runs were designated as Samples A and B, respectively. Samples were taken of each run and analyzed by gas chromatographic analyses. Table 1 is a summary of the results of the runs. Table 1 identifies (1) the residence time of the vapors in the reactor, in seconds, designated as "Time"; (2) the temperature of the reactor, in ° C., designated as "Temp"; and (3) the analyses of the reactor effluent, as to content, in mole percent of primary cyclopolydimethylsiloxane specie, $D_c$, designated as "%$D_3$", "%$D_4$", "%$D_5$", and "%$D_6$", respectively.

TABLE 1

| Sample | Time | Temp | $D_3$ | $D_4$ | $D_5$ | $D_6$ |
| --- | --- | --- | --- | --- | --- | --- |
| Feed | — | — | — | 97.3 | 2.7 | — |
| A | 410 | 400 | 27.4 | 59.5 | 11.9 | 1.4 |
| B | 210 | 450 | 33.1 | 55.4 | 10.7 | 0.9 |

The above results demonstrate that a feed that is essentially $D_4$ can be equilibrated in the vapor phase to a mixture of $D_c$ with significantly increased levels of $D_3$ and $D_5$.

EXAMPLE 2

Using the apparatus and procedures of Example 1, a series of runs was made using as catalysts alkali metal compounds deposited on charcoal. The alkali metal compound on charcoal was prepared by depositing the appropriate alkali metal compound, at the desired loading, from an aqueous solution on 20 to 40 mesh activated charcoal. The activated charcoal was Mathison 6X 648. The bulk of the water was driven from the catalyst slurry by drying in an air-circulating oven.

Six runs were made, and are designated as Samples C, D. E, F, G, and H, respectively. Pressure in the reactor was again controlled at essentially atmospheric pressure. The $D_x$ feed again was essentially $D_4$. Table 2 is a summary of the results of these runs. The notation in Table 1 are utilized. Additionally, the particular catalyst is identified by the weight percent of the alkali metal compound on charcoal, designated as "Catalyst".

TABLE 2

| Sample | Catalyst | Time | Temp | $D_3$ | $D_4$ | $D_5$ | $D_6$ |
| --- | --- | --- | --- | --- | --- | --- | --- |
| C | 50% KOH | 2.5 | 250 | 10.2 | 67.8 | 19.0 | 2.8 |
| D | 50% KOH | 6.5 | 250 | 10.0 | 66.7 | 20.0 | 3.2 |
| E | 95% $K_2CO_3$ | 2.6 | 300 | 15.6 | 64.9 | 17.2 | 2.3 |
| F | 20% KOH | 1.3 | 350 | 20.9 | 62.5 | 14.9 | 1.8 |
| G | 95% $K_2CO_3$ | 4.2 | 355 | 22.1 | 61.7 | 14.3 | 1.8 |
| H | 20% KOH | 2.8 | 400 | 25.6 | 60.2 | 12.8 | 1.5 |

The above results demonstrate that alkali metal compounds deposited on charcoal are effective catalysts for the vapor phase rearrangement of $D_x$.

EXAMPLE 3

Using the apparatus and procedures of Example 1, a series of 6 runs was made in which the pressure in the reactor was controlled at 100 mm Hg. The catalyst utilized was 20 weight percent KOH on charcoal. The $D_x$ feed again was essentially $D_4$. These runs are designated as Samples J, K, L, M, N, and P, respectively. Table 3 is a summary of the results of these runs. The notation in Table 1 are utilized.

TABLE 3

| Sample | Time | Temp | $D_3$ | $D_4$ | $D_5$ | $D_6$ |
|---|---|---|---|---|---|---|
| J | 5.6 | 150 | 5.6 | 86.4 | 6.6 | 1.4 |
| K | 4.9 | 170 | 6.1 | 76.8 | 15.3 | 1.8 |
| L | 1.1 | 200 | 11.7 | 76.8 | 10.8 | 0.9 |
| M | 0.7 | 250 | 19.1 | 71.0 | 9.4 | 0.5 |
| N | 1.6 | 300 | 25.8 | 63.5 | 10.2 | 0.6 |
| P | 0.9 | 350 | 31.6 | 59.5 | 8.6 | 0.4 |

The above results demonstrate the impact of temperature at a pressure of 100 mm Hg in shifting the distribution of $D_c$ in the vapor phase.

EXAMPLE 4

Using the apparatus and procedures of Example 1, a series of 6 runs was made in which the temperature of the reactor was controlled at 350° C. The catalyst utilized was either KOH or $K_2CO_3$ on activated charcoal. The pressure in the reactor was varied. The $D_x$ feed again was essentially $D_4$. These runs are designated as Samples Q, R, S, T, U, and V, respectively. Table 4 is a summary of the results of these runs. The notation in Table 2 are utilized. Additionally, the reactor pressure, in mm Hg is designated as "Press".

TABLE 4

| Sample | Catalyst | Time | Press | $D_3$ | $D_4$ | $D_5$ | $D_6$ |
|---|---|---|---|---|---|---|---|
| Q | 20% KOH | 1.0 | 114 | 31.6 | 59.5 | 8.6 | 0.4 |
| R | 20% KOH | 1.3 | 760 | 20.9 | 62.5 | 14.9 | 1.8 |
| S | 95% $K_2CO_3$ | 8.6 | 965 | 21.7 | 64.1 | 12.8 | 1.3 |
| T | 95% $K_2CO_3$ | 13.9 | 1504 | 19.5 | 64.0 | 14.3 | 2.1 |
| U | 95% $K_2CO_3$ | 21.3 | 2280 | 17.0 | 63.0 | 15.9 | 3.0 |
| V | 95% $K_2CO_3$ | 44.8 | 3085 | 15.6 | 64.6 | 16.5 | 3.0 |

The above results demonstrate the impact of pressure on the equilibrium content of $D_c$ in the vapor phase.

EXAMPLE 5

Using apparatus and procedures similar to Example 1, a series of 5 runs was made evaluating various alkali metal compounds deposited on activated charcoal. The activated charcoal utilized was Calgon BCP. 12×30 mesh. purchased from Calgon. The alkali metal compounds deposited on charcoal were prepared in a manner similar to that described in Example 2. The bulk of the water was driven from the catalyst slurry by drying the slurry in an aircirculating oven at a temperature of 145° C. for 16 hours. In each run the reactor was heated to about 250° C. and purged for one hour with nitrogen gas before $D_x$ feed was begun. The feed $D_x$ was $D_4$. Temperature in the reactor was controlled at about 250° C. Pressure in the reactor was controlled at about 760 mm Hg. Residence time of the vapors in the reactor was controlled at about 1 second.

The 5 runs are designated as Samples AA, BB, CC, DD, and EE, respectively. Table 5 is a summary of the results of this series of runs. The notation used in the previous examples is used in Table 5 with the exception that $D_c$ content is in weight percent. $D_c$ content in subsequent examples is reported in weight percent.

TABLE 5

| Sample | Catalyst | $D_3$ | $D_4$ | $D_5$ | $D_6$ |
|---|---|---|---|---|---|
| AA | 10% $Cs_2CO_3$ | 7.3 | 69.7 | 18.8 | 4.2 |
| BB | 3.4% $K_2CO_3$/KOH | 7.9 | 72.5 | 16.0 | 3.6 |
| CC | 2.7% CsOH | 7.2 | 71.7 | 17.2 | 3.9 |
| DD | 5% NaOH | 7.9 | 74.5 | 14.6 | 3.0 |
| EE | 3% KOH | 8.0 | 70.0 | 17.2 | 3.7 |

The above results demonstrate that various alkali metal compounds, supported on a carbonaceous material, are effective in shifting the distribution mixture of $D_c$ in the vapor phase.

EXAMPLE 6

Using the apparatus and procedures of Example 5, a series of 4 runs was made to study the effect of the loading of an alkali metal compound on activated charcoal. The alkali metal compounds deposited on charcoal was KOH and was prepared in a manner similar to that described in Examples 2 and 5. The feed $D_x$ was $D_4$. Temperature in the reactor was controlled at about 250° C. Pressure in the reactor was controlled at about 760 mm Hg. Residence time of the vapors in the reactor was controlled at about 1 second.

The 4 runs are designated as Samples FF, GG, HH, and JJ, respectively. Table 6 is a summary of the results of this series of runs. The notation used in the previous examples is used in Table 6. Additionally. the loading of the KOH on the activated charcoal. expressed in weight percent, is designated as "% KOH" in Table 6.

TABLE 6

| Sample | % KOH | $D_3$ | $D_4$ | $D_5$ | $D_6$ |
|---|---|---|---|---|---|
| FF | 1 | 7.5 | 77.4 | 12.6 | 2.5 |
| GG | 2 | 9.3 | 67.6 | 19.4 | 3.7 |
| HH | 3 | 7.9 | 68.1 | 20.0 | 4.0 |
| JJ | 5 | 8.5 | 66.9 | 20.7 | 3.9 |

The above results demonstrate the impact of alkali metal compound concentration on a supported catalyst on the equilibration of $D_c$ in the vapor phase.

EXAMPLE 7

Using the apparatus and procedures of Example 5, a series of 9 runs was made to study the effect of the various solid supports upon which an alkali metal compound could be deposited. The alkali metal compound deposited was KOH and was deposited at a 3 weight percent loading and prepared in a manner similar to that described in Examples 2 and 5. The feed $D_x$ was $D_4$. Temperature in the reactor was controlled at about 250° C. Pressure in the reactor was controlled at about 760 mm Hg. Residence time of the vapors in the reactor was controlled at about 1 second.

The 9 runs are disignated as Samples KK, LL, MM, NN, PP, QQ, RR, SS and TT, respectively. Table 7 is a summary description of the solid supports utilized in this study. Table 7 identifies the solid support, designated as "Support"; the geometric form of the solid support is designated as "Form"; the dimensions of the solids, if available, are designated as "Size".

TABLE 7

| Sample | Support | Form | Size |
| --- | --- | --- | --- |
| KK | Charcoal | Granules | 12 × 30 mesh |
| LL | Charcoal | Granules | 12 × 40 mesh |
| MM | Charcoal | Granules | 12 × 30 mesh |
| NN | Molecular Sieves | Pellets | ⅛", 10 A pores |
| PP | Glass Microspheres | Spheres | 30–120 microns |
| QQ | Glass Beads | Beads | 4 mm |
| RR | Steel Packing | Chips | |
| SS | Activated Clay | Granules | |
| TT | Silica Gel | Granules | |

The charcoal used in Samples KK, LL, and MM were purchased from Calgon. The charcoal from Samples KK and LL are produced from coal. The charcoal from Sample MM is produced from coconut shells. The molecular sieves from Sample NN are Linde 13X molecular sieves. The glass microspheres were purchase from 3M. The glass beads were purchased from VWR Scientific. The activated clay was Filtrol 25. 10×20 mesh, purchased from Harshaw-Filtrol. The silica gel was purchased from W. R. Grace, Davison Chemical Division.

Table 8 is a summary of the results of this series of runs. The notation used in the previous examples is used in Table 8.

TABLE 8

| Sample | Time | $D_3$ | $D_4$ | $D_5$ | $D_6$ |
| --- | --- | --- | --- | --- | --- |
| KK | 1.3 | 7.9 | 68.1 | 20.0 | 4.0 |
| LL | 1.3 | 7.9 | 67.2 | 21.1 | 3.9 |
| MM | 1.3 | 8.0 | 70.0 | 17.2 | 3.7 |
| NN | 1.3 | 0.2 | 90.5 | 8.6 | 0.1 |
| PP | 1.4 | 0.5 | 90.3 | 8.7 | — |
| QQ | 2.9 | 0.6 | 91.2 | 8.1 | 0.1 |
| RR | 1.3 | 0.8 | 92.0 | 7.1 | — |
| SS | 1.3 | 0.7 | 91.7 | 7.4 | — |
| TT | 3.9 | 0.6 | 92.6 | 7.2 | — |

The above results demonstrate that, under the conditions studied, a carbonaceous support is the only material that will yield a supported catalyst effective in the vapor phase rearrangement of $D_c$.

EXAMPLE 8

An extended run on a larger-scale reactor was carried out to study the impact of water content of the feed cyclic siloxanes. While larger in size, the apparatus and procedures utilized were similar to those of the preceding examples. The catalyst was 5 weight percent KOH on charcoal. The charcoal was a 6×16 mesh material purchased from Calgon. The reactor conditions were maintained at 250° C. at atmospheric pressure. The feed cyclic siloxanes were essentially $D_4$.

The feed cyclic siloxanes had an average water content of 25 ppm. The reactor system was run for an extended period of time. Product distribution began to drift back toward $D_4$. The product distribution after this time is designated as Sample UU. The water content of the feed was increased to about 100 ppm by addition of water. Shortly after the addition of the water, the reactor effluent was sampled. This sample is designated Sample VV.

Table 9 is a summary of the analysis of reactor effluent after operation at low water content and reactor effluent after addition of water to the feed. In Table 9, the total water content of the feed is designated as "ppm water"; cyclic content is noted using the designation of the preceding example.

TABLE 9

| Sample | ppm Water | $D_3$ | $D_4$ | $D_5$ | $D_6$ |
| --- | --- | --- | --- | --- | --- |
| UU | 25 | 6.2 | 84.8 | 6.5 | 2.1 |
| VV | 100 | 7.2 | 71.8 | 16.7 | 3.5 |

The above results demonstrated the beneficial effect of additional water upon the performance of the catalyst.

What is claimed is:

1. A process for preparing a product cyclopolydiorganosiloxane, $$(R_2SiO)_c,$$

wherein each R is independently selected from a group consisting of alkyl groups, alkenyl groups, aryl groups, and alkaryl groups; and c has a value of 3, 4, 5, 6, 7, 8, or 9,
said process comprising
(A) vaporizing a feed material consisting of a cyclopolydiorganosiloxane having the formula, $$(R_2SiO)_x$$

wherein each R is defined above; and x is 3, 4, 5, 6, 7, 8, or 9, or a mixture of said cyclopolydiorganosiloxanes,
(B) passing vapors of the feed material through a heated bed of a solid catalyst, said catalyst comprising an alkali metal compound;
(C) controlling pressure and temperature in the heated catalyst bed to favor formation of $(R_2SiO)_c$ in an equilibrating mixture with other cyclopolydiorganosiloxanes; and
(D) recovering an amount of the product cyclopolydiorganosiloxane, $(R_2SiO)_c$, which is substantially increased from the amount present in the feed material.

2. A process according to claim 1, wherein the alkali metal compound is selected from a group consisting of sodium hydroxide, sodium carbonate, potassium hydroxide, potassium carbonate, cesium hydroxide, and cesium carbonate.

3. A process according to claim 1, wherein the catalyst is an alkali metal compound on a carbonaceous support.

4. A process according to claim 3, wherein the carbonaceous support is selected from a group consisting of activated carbon, coke, and charcoal.

5. A process according to claim 3, wherein the alkali metal compound is present at greater than about one percent of the weight of the catalyst.

6. A process according to claim 1, wherein temperature in the heated bed of solid catalyst is greater than the dew point of the feed material.

7. A process according to claim 1, wherein time required for the vapors to pass through the heated bed of solid catalyst is greater than about 0.5 seconds.

8. A process according to claim 1, wherein total water content of the feed material is in a range from about 50 to 100 parts per million on a weight basis.

9. A process according to claim 8, wherein additional water is fed with the feed cyclopolydiorganosiloxane material.

10. A process according to claim 1, wherein $(R_2SiO)_c$ is recovered by distillation.

11. A process according to claim 1, wherein the feed material is $[(CH_3)_2SiO]_x$ or a mixture thereof; wherein the solid catalyst is potassium hydroxide deposited on charcoal, said potassium hydroxide content of the catalyst being greater than about one weight percent; wherein the temperature in the heated bed of solid catalyst is greater than about 300° C.; wherein the pressure in the heated bed of solid catalyst is less than about 10 mm Hg.; wherein the time required for the vapors to pass through the heated bed of solid catalyst is greater than about 0.5 seconds; and wherein an amount of $[(CH_3)_2SiO]_3$ substantially increased from the amount present in the feed material is recovered.

12. A process according to claim 11, wherein the total water content of the feed material is in a range from about 50 to 100 parts per million by weight; wherein the potassium hydroxide content of the catalyst is in a range from about 1 to 5 weight percent; wherein the temperature in the heated bed of solid catalyst is in a range of about 300° to 450° C. wherein the pressure in the heated bed of solid catalyst is in a range from about 5 to 10 mm Hg.; wherein the time required for the vapors to pass through the heated bed of solid catalyst is in a range from about 1 to 6 seconds; and wherein $[(CH_3)_2SiO]_3$ is recovered at a purity greater than about 95 weight percent by distillation.

13. A process according to claim 1, wherein the feed material is $[(CH_3)_2SiO]_x$ or a mixture thereof; wherein the solid catalyst is potassium hydroxide deposited on charcoal, said potassium hydroxide content of the catalyst being greater than about one weight percent; wherein the temperature in the heated bed of solid catalyst is about 200° C.; wherein the pressure in the heated bed of solid catalyst bed is about 100 mm Hg.; wherein the time required for the vapors to pass through the heated bed of solid catalyst is greater than about 0.5 seconds; and wherein an amount of $[(CH_3)_2SiO]_4$ substantially increased from the amount present in the feed material is recovered.

14. A process according to claim 13, wherein the total water content of the feed material is in a range from about 50 to 100 parts per million by weight; wherein the potassium hydroxide content of the catalyst is in a range from about 1 to 5 weight percent; wherein the time required for the vapors to pass through the heated bed of solid catalyst is in a range from about 1 to 6 seconds; and wherein $[(CH_3)_2SiO]_4$ is recovered at a purity greater than about 95 weight percent by distillation.

15. A process according to claim 1, wherein the feed material is $[(CH_3)_2SiO]_x$ or a mixture thereof; wherein the solid catalyst is potassium hydroxide deposited on charcoal said potassium hydroxide content of the catalyst being greater than about one weight percent; wherein the temperature in the heated bed of solid catalyst is greater than about 200° C.; wherein the pressure in the heated bed of solid catalyst is greater than about 400 mm Hg.; wherein the time required for the vapors to pass through the heated bed of solid catalyst is greater than about 0.5 seconds; and wherein amounts of $[(CH_3)_2SiO]_5$ and $[(CH_3)_2SiO]_6$ substantially increased from the amounts present in the feed material are recovered.

16. A process according to claim 15, wherein the total water content of the feed material is in a range from about 50 to 100 parts per million by weight; wherein the potassium hydroxide content of the catalyst is in a range from about 1 to 5 weight percent; wherein the temperature in the heated bed of solid catalyst is in a range from about 200° to 300° C.; wherein the pressure in the heated bed of solid catalyst is in a range from about 500 to 1500 mm Hg.; wherein the time required for the vapors to pass through the bed of solid catalyst is in a range from about 1 to 6 seconds; and wherein $[(CH_3)_2SiO]_5$ and $[(CH_3)_2SiO]_6$ are recovered at purities greater than about 95 weight percent by distillation.

* * * * *